US012662642B2

(12) United States Patent
Matsubara et al.

(10) Patent No.: US 12,662,642 B2
(45) Date of Patent: Jun. 23, 2026

(54) LUBRICANT BASE OIL

(71) Applicant: IDEMITSU KOSAN CO., LTD., Tokyo (JP)

(72) Inventors: Kazushige Matsubara, Tokyo (JP); Hiroyuki Tatsumi, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 18/685,677

(22) PCT Filed: Jul. 25, 2022

(86) PCT No.: PCT/JP2022/028573
§ 371 (c)(1),
(2) Date: Feb. 22, 2024

(87) PCT Pub. No.: WO2023/026739
PCT Pub. Date: Mar. 2, 2023

(65) Prior Publication Data

US 2024/0425772 A1 Dec. 26, 2024

(30) Foreign Application Priority Data

Aug. 26, 2021 (JP) ................................ 2021-137996

(51) Int. Cl.

| | |
|---|---|
| ***C10M 105/34*** | (2006.01) |
| ***C07C 53/126*** | (2006.01) |
| *C10N 20/00* | (2006.01) |
| *C10N 20/02* | (2006.01) |

(52) U.S. Cl.
CPC ......... *C10M 105/34* (2013.01); *C07C 53/126* (2013.01); *C10M 2207/2815* (2013.01); *C10N 2020/02* (2013.01); *C10N 2020/071* (2020.05)

(58) Field of Classification Search
CPC ............... C07C 53/126; C10M 105/34; C10M 2207/2815; C10N 2020/071; C10N 2020/02
See application file for complete search history.

(56) References Cited

U.S. PATENT DOCUMENTS

| | | | | |
|---|---|---|---|---|
| 2011/0207638 | A1* | 8/2011 | Singh ................. | C10M 169/048 508/282 |
| 2011/0220845 | A1 | 9/2011 | Packet et al. | |
| 2013/0190217 | A1 | 7/2013 | Lammie et al. | |
| 2021/0230096 | A1 | 7/2021 | Urata et al. | |
| 2022/0333029 | A1 | 10/2022 | Scherer et al. | |

FOREIGN PATENT DOCUMENTS

| | | | |
|---|---|---|---|
| DE | 10 2015 112 655 | A1 | 2/2017 |
| EP | 3 178 907 | A1 | 6/2017 |
| JP | 2009-203275 | A | 9/2009 |
| JP | 2014-043526 | A | 3/2014 |
| JP | 2014-139306 | | 7/2014 |
| JP | 2016-536409 | A | 11/2016 |
| JP | 2017-515965 | A | 6/2017 |
| JP | 2021-20993 | A | 2/2021 |
| JP | 2021-025025 | A | 2/2021 |
| WO | WO 2015/027035 | A1 | 2/2015 |
| WO | WO 2015/174992 | A1 | 11/2015 |
| WO | WO 2019/211934 | A1 | 11/2019 |
| WO | WO 2021/063759 | A1 | 4/2021 |

OTHER PUBLICATIONS

International Search Report and Written Opinion issued on Sep. 6, 2022 in PCT/JP2022/028573, filed on Jul. 25, 2022, 11 pages (with English Translation).
Oh, Jinho et al., Synthesis of biolubricants using sulfated zirconia catalysts, Applied Catalysis A: General, 2013, vol. 455, pp. 164-171.
Azcan, Nezihe et al., Obraining 2-Octanol, 2-Octanone, and Sebacic Acid from Castor Oil by Microwave-Induced Alkali Fusion, Ind. Eng. Chem. Res., 2008, vol. 47, pp. 1774-1778.
Office Action issued Apr. 15, 2025, in Japanese Application No. 2021-137996 with machine English translation (5 pages).
Decision of Refusal issued Sep. 2, 2025, in Japanese Application No. 2021-137996 with machine English translation (6 pages).
Supplementary European Search Report issued Jun. 30, 2025, in European Application No. 22861030.9.

* cited by examiner

*Primary Examiner* — Vishal V Vasisth
(74) *Attorney, Agent, or Firm* — Oblon, McClelland, Maier & Neustadt, L.L.P.

(57) ABSTRACT

A lubricant base oil having a natural origin content (ISO 16128) of 100%, may contain a monoester compound having one or more branched structures and 18 or more carbon atoms. The monoester compound may a compound of formula (1):

(1)

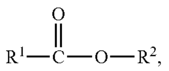

wherein $R^1$ and $R^2$ are each independently a hydrocarbon group, at least one of $R^1$ and $R^2$ is a branched hydrocarbon group, and a total number of carbon atoms of $R^1$ and $R^2$ is 17 or more. In the compound of formula (1), $R^1$ may be an alkyl group or alkenyl group having 8 or more carbon atoms, $R^2$ may be an alkyl group or alkenyl group having 5 or more carbon atoms, and at least one of $R^1$ and $R^2$ may be a branched alkyl group or a branched alkenyl group

18 Claims, No Drawings

LUBRICANT BASE OIL

CROSS-REFERENCE TO RELATED APPLICATIONS

The present application is the national stage of international application PCT/JP2022/028573, filed on Jul. 25, 2022, and claims the benefit of the filing date of Japanese Appl. No. 2021-137996, filed on Aug. 26, 2021.

TECHNICAL FIELD

The present invention relates to a lubricant base oil, and a lubricating oil composition containing the lubricant base oil.

BACKGROUND ART

In recent years, lubricating oil compositions used in automobiles have been developed in consideration of environmental impact. For example, Patent Literature 1 discloses a lubricating oil composition in which the structure and content of polymer components, the evaporation loss according to NOACK, and the content of fraction with a boiling point in the range of 350 to 400° C. are adjusted, for the purpose of reducing fuel consumption in order to reduce carbon dioxide emissions.

CITATION LIST

Patent Literature

Patent Literature 1: JP-A-2021-25025

SUMMARY OF INVENTION

Technical Problem

Meanwhile, it is becoming necessary to consider the environmental impact of lubricating oil compositions not only upon application but also upon disposal from the viewpoint of life cycle assessment. Therefore, there is a demand for a lubricant base oil that can be used to prepare a lubricating oil composition that is excellent in various lubricating properties while reducing the environmental impact upon disposal.

Solution to Problem

The present invention provides a lubricant base oil having a natural origin content (ISO 16128) of 100%, comprising a monoester compound having one or more branched structures and 18 or more carbon atoms, and a lubricating oil composition comprising the lubricant base oil.

Specifically, provided are the lubricant base oil and lubricating oil composition according to the aspects [1] to [8] below.

[1] A lubricant base oil having a natural origin content (ISO 16128) of 100%, comprising a monoester compound having one or more branched structures and 18 or more carbon atoms.

[2] The lubricant base oil according to [1] above, wherein the monoester compound is a compound represented by the general formula (1) below:

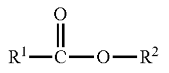

(1)

wherein $R^1$ and $R^2$ are each independently a hydrocarbon group, at least one of $R^1$ and $R^2$ is a branched hydrocarbon group, and the total number of carbon atoms of $R^1$ and $R^2$ is 17 or more.

[3] The lubricant base oil according to [2] above, wherein, in the general formula (1), $R^1$ is an alkyl group or alkenyl group having 8 or more carbon atoms, $R^2$ is an alkyl group or alkenyl group having 5 or more carbon atoms, and at least one of $R^1$ and $R^2$ is a branched alkyl group or a branched alkenyl group.

[4] The lubricant base oil according to [2] or [3] above, wherein $R^1$ and $R^2$ in formula (1) above are each independently a branched alkyl group or a branched alkenyl group.

[5] The lubricant base oil according to any one of [1] to [4], wherein the pour point of the lubricant base oil is 0° C. or less.

[6] The lubricant base oil according to any one of [1] to [5], wherein the volume change rate of an acrylic rubber for test, as measured by immersing the acrylic rubber for test in the lubricant base oil under conditions at 150° C. for 72 hours in accordance with JIS K6258, is less than 20%.

[7] A lubricating oil composition comprising the lubricant base oil according to any one of [1] to [6].

[8] The lubricating oil composition according to [7] above, further comprising one or more additives for lubricating oil selected from a pour point depressant, a viscosity index improver, an antioxidant, an extreme pressure agent, a metallic detergent, an ashless dispersant, a metal deactivator, a friction modifier, a rust inhibitor, and a defoamer.

Advantageous Effects of Invention

The lubricant base oil according to a preferable aspect of the present invention allows a lubricating oil composition that is excellent in various lubricating properties to be prepared, while reducing the environmental impact upon disposal.

DESCRIPTION OF EMBODIMENTS

For the numerical ranges described herein, any upper limit and lower limit can be combined. For example, in the case where "preferably 30 to 100, more preferably 40 to 80" is described as numerical ranges, the range of "30 to 80" and the range of "40 to 100" are also included in the numerical ranges disclosed in this description.

Further, for example, in the case where "preferably 30 or more, more preferably 40 or more, further preferably 100 or less, more preferably 80 or less" is described as numerical ranges, the range of "30 to 80" and the range of "40 to 100" are also included in the numerical ranges disclosed in this description.

In addition, the description "60 to 100" as a numerical range disclosed in this description, for example, means the range of "60 or more and 100 or less".

As used herein, kinematic viscosity and viscosity index mean values measured or calculated in accordance with JIS K2283:2000.

Configuration of Lubricant Base Oil

The lubricant base oil according to an aspect of the present invention has a natural origin content (ISO 16128) of 100% and comprises a monoester compound having one or more branched structures and 18 or more carbon atoms.

As used herein, the natural origin content is a value calculated in accordance with ISO 16128 and indicates a percentage of natural raw materials derived from plants, animals, algae, microorganisms such as bacteria and fungi, and minerals in the raw materials used for the production of the lubricant base oil.

That is, since the lubricant base oil according to an aspect of the present invention has a natural origin content of 100% calculated in accordance with ISO 16128, all the raw materials are derived from natural raw materials.

For example, in the automotive industry, lubricating oil compositions are required to reduce the environmental impact upon disposal from the viewpoint of life cycle assessment.

The lubricant base oil according to an aspect of the present invention is composed of raw materials so that the natural origin content (ISO 16128) is 100%, for reducing the environmental impact upon disposal.

When the lubricant base oil according to an aspect of the present invention is composed of raw materials derived from plants, even if carbon dioxide is generated by combustion upon disposal, the carbon dioxide in the atmosphere does not increase over the entire life cycle, since the plants constituting the raw materials absorb carbon dioxide during the growth process, so that the balance of carbon dioxide emissions will be treated as "carbon neutral", meaning substantially zero.

The lubricant base oil according to an aspect of the present invention is composed of a monoester compound.

The monoester compound can be produced by an ester reaction between a monocarboxylic acid component and an alcohol component.

2-Ethylhexyl palmitate, which is described in Patent Literature 1 and the like and is generally known as a lubricating base oil, is produced by an ester reaction between palmitic acid and 2-ethylhexanol, but 2-ethylhexanol is a raw material derived from petroleum and does not correspond to the natural raw material specified in ISO 16128. Therefore, the natural origin content of 2-ethylhexyl palmitate is not 100%.

Meanwhile, since the lubricant base oil according to an aspect of the present invention has a natural origin content (ISO 16128) of 100%, both the monocarboxylic acid component and the alcohol component as raw materials of the monoester compound are required to be derived from natural raw materials. As a result, the lubricant base oil according to an aspect of the present invention can be a lubricant base oil with reduced environmental impact upon disposal.

Further, for making the lubricant base oil treated as carbon neutral, the lubricant base oil according to an aspect of the present invention is preferably composed of a monoester compound produced from a monocarboxylic acid component and an alcohol component that are derived from plants.

Further, the lubricant base oil according to an aspect of the present invention comprises a monoester compound having one or more branched structures and 18 or more carbon atoms. The lubricant base oil can be excellent in various properties (such as viscometric property, pour point, flash point, and rubber swelling resistance) required as a lubricant base oil by comprising the monoester compound having such structures. Therefore, the lubricating oil composition can be excellent in various lubricating properties by using the lubricant base oil.

In the lubricant base oil according to an aspect of the present invention, the monoester compound may have one or more branched structures. For achieving a lubricant base oil with a lower pour point, the monoester compound preferably has two or more branched structures, more preferably two to five branched structures, further preferably two branched structures.

In the lubricant base oil according to an aspect of the present invention, the number of carbon atoms in the monoester compound may be 18 or more. For achieving a lubricant base oil with a higher viscosity, a higher flash point, and further improved rubber swelling resistance, it may be preferably 19 or more, more preferably 20 or more, more preferably 21 or more, further preferably 22 or more, further preferably 23 or more, furthermore preferably 24 or more, particularly preferably 25 or more, and 70 or less, 65 or less, 60 or less, 55 or less, 50 or less, 48 or less, 46 or less, 45 or less, 44 or less, 42 or less, 40 or less, 38 or less, 37 or less, 36 or less, 35 or less, 34 or less, 33 or less, 32 or less, 31 or less, 30 or less, 29 or less, or 28 or less.

The lubricant base oil according to an aspect of the present invention has a natural origin content of 100% and may contain a compound other than the monoester compound within a range that does not inhibit various properties as a lubricant base oil.

However, for achieving a lubricant base oil that is excellent in various properties (such as viscometric property, pour point, flash point, and rubber swelling resistance), the content ratio of the monoester compound contained in the lubricant base oil according to an aspect of the present invention is preferably 50 to 100 mass %, more preferably 60 to 100 mass %, more preferably 70 to 100 mass %, further preferably 80 to 100 mass %, further preferably 85 to 100 mass %, furthermore preferably 90 to 100 mass %, furthermore preferably 95 to 100 mass %, particularly preferably 98 to 100 mass %, based on the total amount (100 mass %) of the lubricant base oil.

In the lubricant base oil according to an aspect of the present invention, for achieving a lubricant base oil that is excellent in various properties (such as viscometric property, pour point, flash point, and rubber swelling resistance), the monoester compound is preferably a compound represented by the general formula (1) below.

(1)

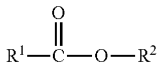

In the general formula (1) above, $R^1$ and $R^2$ are each independently a hydrocarbon group, and at least one of $R^1$ and $R^2$ is a branched hydrocarbon group.

The branched hydrocarbon group may be a group having one or more branching points, preferably a group having one or two branching points, more preferably a group having one branching point.

Further, the total number of carbon atoms of $R^1$ and $R^2$ is 17 or more, but for achieving a lubricant base oil with a higher viscosity, a higher flash point, and further improved rubber swelling resistance, it may be preferably 18 or more, more preferably 19 or more, more preferably 20 or more, further preferably 21 or more, further preferably 22 or more, furthermore preferably 23 or more, particularly preferably 24 or more, and 70 or less, 65 or less, 60 or less, 55 or less, 50 or less, 48 or less, 46 or less, 45 or less, 44 or less, 42 or less, 40 or less, 38 or less, 37 or less, 36 or less, 35 or less, 34 or less, 33 or less, 32 or less, 31 or less, 30 or less, 29 or less, 28 or less, or 27 or less.

For achieving a lubricant base oil with a higher viscosity, a higher flash point, and further improved rubber swelling resistance, the number of carbon atoms in $R^1$ in the general formula (1) above may be preferably 8 or more, more preferably 9 or more, more preferably 10 or more, more preferably 11 or more, further preferably 12 or more, further preferably 13 or more, furthermore preferably 14 or more, furthermore preferably 15 or more, particularly preferably 16 or more, and 40 or less, 35 or less, 30 or less, 28 or less, 26 or less, 25 or less, 24 or less, 23 or less, 22 or less, 21 or less, or 20 or less.

For achieving a lubricant base oil with a higher viscosity, a higher flash point, and further improved rubber swelling resistance, the number of carbon atoms in $R^2$ in the general formula (1) above may be preferably 5 or more, more preferably 6 or more, further preferably 7 or more, furthermore preferably 8 or more, and 30 or less, 25 or less, 22 or less, 20 or less, 18 or less, 16 or less, 15 or less, 14 or less, 13 or less, or 12 or less.

Examples of the hydrocarbon group that can be selected as $R^1$ and $R^2$ include an alkyl group, an alkenyl group, a cycloalkyl group, an aryl group, an alkylaryl group, and an arylalkyl group.

Examples of the alkyl group include a linear alkyl group or a branched alkyl group such as a methyl group, an ethyl group, a propyl group (a n-propyl group and an isopropyl group), a butyl group (a n-butyl group, a s-butyl group, a t-butyl group, and an isobutyl group), a pentyl group, a hexyl group, a heptyl group, an octyl group, a 2-ethylhexyl group, a 1-methylheptyl group, nonyl group, a 1-methyloctyl group, a 1,1-dimethylheptyl group, a decyl group, a 1-methylheptyl group, an undecyl group, a 1-methyldecyl group, a dodecyl group, a 1-methylundecyl group, a tridecyl group, a 1-methyldodecyl group, a tetradecyl group, a 1-methyltridecyl group, a pentadecyl group, a 1-methyltetradecyl group, a hexadecyl group, a 1-methylpentadecyl group, a heptadecyl group, a 1-methylhexadecyl group, an octadecyl group, a 1-methylheptadecyl group, a nonadecyl group, and a 1-methyloctadecyl group.

Examples of the alkenyl group include linear alkenyl groups or branched alkenyl groups such as an ethenyl group, a propenyl group, a butenyl group, a pentenyl group, a hexenyl group, a heptenyl group, an octenyl group, a methylheptenyl group, a nonyl group, a methyloctenyl group, a decenyl group, a methylnonyl group, an undecenyl group, a methyldecenyl group, a dodecenyl group, a methylundecenyl group, a tridecenyl group, a methyldodecenyl group, a tetradecenyl group, a methyltridecenyl group, a pentadecenyl group, a methyltetradecenyl group, a hexadecenyl group, a methylpentadecenyl group, a heptadecenyl group, a methylhexadecenyl group, an octadecenyl group, a methylheptadecenyl group, a nonadecenyl group, and a methyloctadecenyl group.

Examples of the cycloalkyl group include a cycloalkyl group that may have an alkyl group such as a cyclohexyl group, a dimethylcyclohexyl group, an ethylcyclohexyl group, a propylcyclohexyl group, a butylcyclohexyl group, and a heptylcyclohexyl group.

Examples of the aryl group include a phenyl group, a naphthyl group, an anthracenyl group, a biphenyl group, and a tarphenyl group.

Examples of the alkylaryl group include a tolyl group, a dimethylphenyl group, a butylphenyl group, a nonylphenyl group, a methylbenzyl group, and a dimethylnaphthyl group.

Examples of the arylalkyl group include a phenylmethyl group, a phenylethyl group, and a diphenylmethyl group.

Among these, for achieving a lubricant base oil that is more excellent in various properties (such as viscometric property, pour point, flash point, and rubber swelling resistance), it is preferable that, in the general formula (1) above, $R^1$ and $R^2$ are each independently an alkyl group or alkenyl group, and at least one of $R^1$ and $R^2$ is a branched alkyl group or a branched alkenyl group, and it is more preferable that $R^1$ and $R^2$ are each independently an alkyl group, and at least one of $R^1$ and $R^2$ is a branched alkyl group.

Further, in the lubricant base oil according to an aspect of the present invention, for achieving a lubricant base oil that is more excellent in various properties (particularly, viscometric property, flash point, and rubber swelling resistance), it is preferable that, in the general formula (1) above, $R^1$ is an alkyl group or alkenyl group having 8 or more carbon atoms, $R^2$ is an alkyl group or alkenyl group having 5 or more carbon atoms, and at least one of $R^1$ and $R^2$ is a branched alkyl group or branched alkenyl group, and it is more preferable that $R^1$ is an alkyl group having 8 or more carbon atoms, $R^2$ is an alkyl group having 5 or more carbon atoms, and at least one of $R^1$ and $R^2$ is a branched alkyl group.

In such an aspect, the number of carbon atoms in $R^1$ is 8 or more, but for achieving a lubricant base oil with a higher flash point and further improved rubber swelling resistance, it is preferably 9 or more, more preferably 10 or more, more preferably 11 or more, more preferably 12 or more, further preferably 13 or more, further preferably 14 or more, furthermore preferably 15 or more, particularly preferably 16 or more, and 40 or less, 35 or less, 30 or less, 28 or less, 26 or less, 25 or less, 24 or less, 23 or less, 22 or less, 21 or less, or 20 or less.

Further, in the aspect, the number of carbon atoms in $R^2$ is 5 or more, but for achieving a lubricant base oil with a higher viscosity, a higher flash point, and further improved rubber swelling resistance, it is preferably 6 or more, more preferably 7 or more, further preferably 8 or more, and 30 or less, 25 or less, 22 or less, 20 or less, 18 or less, 16 or less, 15 or less, 14 or less, 13 or less, or 12 or less.

In the lubricant base oil according to an aspect of the present invention, particularly, for achieving a lubricant base oil with a lower pour point, $R^1$ and $R^2$ in the general formula (1) above are preferably each independently a branched alkyl group or a branched alkenyl group, more preferably a branched alkyl group.

[Properties of Lubricant Base Oil]

The lubricant base oil according to an aspect of the present invention may have a kinematic viscosity at 40° C. of 4.0 $mm^2/s$ or more, 4.2 $mm^2/s$ or more, 4.5 $mm^2/s$ or more, 4.7 $mm^2/s$ or more, 5.0 $mm^2/s$ or more, 5.2 $mm^2/s$ or more, 5.5 $mm^2/s$ or more, 5.7 $mm^2/s$ or more, 6.0 $mm^2/s$ or more, 6.2 $mm^2/s$ or more, 6.5 $mm^2/s$ or more, 6.7 $mm^2/s$ or more, 7.0 $mm^2/s$ or more, 7.5 $mm^2/s$ or more, 8.0 $mm^2/s$ or more, 8.5 $mm^2/s$ or more, 9.0 $mm^2/s$ or more, or 9.5 $mm^2/s$ or more, and 100 $mm^2/s$ or less, 90 $mm^2/s$ or less, 80 $mm^2/s$ or less, 70 $mm^2/s$ or less, 60 $mm^2/s$ or less, 50 $mm^2/s$ or less, 40 $mm^2$/s or less, 35 $mm^2$/s or less, 30 $mm^2$/s or less, 25 $mm^2$/s or less, or 20 $mm^2$/s or less.

The lubricant base oil according to an aspect of the present invention may have a kinematic viscosity at 100° C. of 1.0 $mm^2$/s or more, 1.2 $mm^2$/s or more, 1.5 $mm^2$/s or more, 1.7 $mm^2$/s or more, 2.0 $mm^2$/s or more, 2.2 $mm^2$/s or more, 2.5 $mm^2$/s or more, 2.7 $mm^2$/s or more, or 3.0 $mm^2$/s or more, and 10 $mm^2$/s or less, 9.0 $mm^2$/s or less, 8.0 $mm^2$/s or less, 7.0 $mm^2$/s or less, 6.0 $mm^2$/s or less, 5.0 $mm^2$/s or less, 4.5 $mm^2$/s or less, 4.2 $mm^2$/s or less, 4.0 $mm^2$/s or less, 3.8 $mm^2$/s or less, or 3.5 $mm^2$/s or less.

The lubricant base oil according to an aspect of the present invention may have a viscosity index of 70 or more, 80 or more, 85 or more, 90 or more, 95 or more, 100 or more, 105 or more, 110 or more, 115 or more, 120 or more, 125 or more, or 130 or more.

For achieving a lubricant base oil that can be easily prepared into a lubricating oil composition that can be used in a wide temperature range, the lubricant base oil according to an aspect of the present invention preferably has a pour point of 0° C. or less, more preferably −5° C. or less, more preferably −10° C. or less, further preferably −20° C. or less, further preferably −25° C. or less, furthermore preferably −30° C. or less, furthermore preferably −35° C. or less, particularly preferably −40° C. or less.

As used herein, the pour point means a value measured in accordance with JIS K2269.

The lubricant base oil according to an aspect of the present invention may have a flash point of preferably 170° C. or more, more preferably 174° C. or more, more preferably 180° C. or more, more preferably 184° C. or more, further preferably 190° C. or more, further preferably 194° C. or more, further preferably 200° C. or more, furthermore preferably 204° C. or more, furthermore preferably 210° C. or more, furthermore preferably 214° C. or more, particularly preferably 220° C. or more, and 400° C. or less, 380° C. or less, 350° C. or less, 330° C. or less, 320° C. or less, 310° C. or less, or 300° C. or less.

As used herein, the flash point means a value measured by the Cleveland Open Cup method (COC method) in accordance with JIS K2265-4 (Determination of flash point—Part 4: Cleveland open cup method).

The volume change rate of an acrylic rubber for test, as measured by immersing the acrylic rubber for test in the lubricant base oil according to an aspect of the present invention under conditions at 150° C. for 72 hours in accordance with JIS K6258 is preferably less than 20%, more preferably 18% or less, more preferably 15% or less, further preferably 13% or less, further preferably 10% or less, furthermore preferably 8% or less, particularly preferably 7% or less, for achieving a lubricant base oil with good rubber swelling resistance.

As used herein, the volume change rate of the acrylic rubber for test means a value measured and calculated by the method described in Examples.

[Configuration of Lubricating Oil Composition]

The lubricating oil composition according to an aspect of the present invention comprises the lubricant base oil according to an aspect of the present invention.

The lubricating oil composition according to an aspect of the present invention may further contain additives for lubricating oil. Specifically, it may further contain one or more additives for lubricating oil selected from a pour point depressant, a viscosity index improver, an antioxidant, an extreme pressure agent, a metallic detergent, an ashless dispersant, a metal deactivator, a friction modifier, a rust inhibitor, and a defoamer.

One of these additives for lubricating oil may be used alone, or two or more of them may be used in combination.

The content of such an additive for lubricating oil can be appropriately adjusted, as long as the effects of the present invention are not impaired, but is generally 0.001 to 15 mass %, preferably 0.005 to 10 mass %, more preferably 0.01 to 5 mass %, independently for each additive, based on the total amount (100 mass %) of the lubricating oil composition.

In the lubricating oil composition according to an aspect of the present invention, the content of the lubricant base oil according to an aspect of the present invention is preferably 50 mass % or more, more preferably 60 mass % or more, further preferably 70 mass % or more, furthermore preferably 80 mass % or more, particularly preferably 90 mass % or more, based on the total amount (100 mass %) of the lubricating oil composition.

[Pour Point Depressant]

Examples of the pour point depressant to be used in an aspect of the present invention include ethylene-vinyl acetate copolymer, a condensate of chlorinated paraffin and naphthalene, a condensate of chlorinated paraffin and phenol, polymethacrylate, and polyalkylstyrene.

One of these pour point depressants may be used alone, or two or more of them may be used in combination.

[Viscosity Index Improver]

Examples of the viscosity index improver to be used in an aspect of the present invention include polymers such as non-dispersed polymethacrylates, dispersed polymethacrylates, olefin copolymers (e.g., ethylene-propylene copolymer), dispersed olefin copolymers, styrene copolymers (e.g., styrene-diene copolymer and styrene-isoprene copolymer).

One of these viscosity index improvers may be used alone, or two or more of them may be used in combination.

Further, the weight-average molecular weight (Mw) Of the viscosity index improver to be used in an aspect of the present invention may be 5,000 or more, 7,000 or more, 10,000 or more, 15,000 or more, or 20,000 or more, and 1,000,000 or less, 700,000 or less, 500,000 or less, 300,000 or less, 200,000 or less, 100,000 or less, or 50,000 or less.

[Antioxidant]

Examples of the antioxidant to be used in an aspect of the present invention include amine antioxidants such as alkylated diphenylamine, phenylnaphthylamine, and alkylated phenylnaphthylamine; phenolic antioxidants such as 2,6-di-t-butylphenol, 4,4'-methylenebis(2,6-di-t-butylphenol), isooctyl-3-(3,5-di-t-butyl-4-hydroxyphenyl) propionate, and n-octadecyl-3-(3,5-di-t-butyl-4-hydroxyphenyl) propionate.

One of these antioxidants may be used alone, or two or more of them may be used in combination.

In the lubricating oil composition according to an aspect of the present invention, an amine antioxidant and a phenolic antioxidant are preferably used as antioxidants in combination.

[Extreme Pressure Agent (Antiwear Agent)]

Examples of the extreme pressure agent (antiwear agent) to be used in an aspect of the present invention include such as sulfur-containing compounds such as zinc dithiophosphate; phosphorus-containing compounds such as phosphorous acid esters, phosphoric acid esters, phosphonic acid esters, and amine salts or metal salts thereof; and sulfur-and phosphorus-containing compounds such as thiophosphorous acid esters, thiophosphoric acid esters, thiophosphonic acid esters, and amine salts or metal salts thereof.

One of these extreme pressure agents may be used alone, or two or more of them may be used in combination.

[Metallic Detergent]

Examples of the metallic detergent to be used in an aspect of the present invention include metal salts such as metal sulfonates, metal salicylates, and metal phenates. Further, the metal atom constituting such a metal salt is preferably a metal atom selected from alkali metals and alkaline earth metals, more preferably sodium, calcium, magnesium, or barium, further preferably calcium.

One of these metallic detergents may be used alone, or two or more of them may be used in combination.

In the lubricating oil composition according to an aspect of the present invention, the metallic detergent preferably contains one or more selected from calcium sulfonate, calcium salicylate, and calcium phenate, more preferably calcium sulfonate.

The content ratio of calcium sulfonate is preferably 50 to 100 mass %, more preferably 60 to 100 mass %, further preferably 70 to 100 mass %, furthermore preferably 80 to 100 mass %, based on the total amount (100 mass %) of the metallic detergent contained in the lubricating oil composition.

The base number of the metallic detergent is preferably 0 to 600 mgKOH/g.

However, in the lubricating oil composition according to an aspect of the present invention, the metallic detergent is preferably an overbased metallic detergent having a base number of 100 mgKOH/g or more. The base number of the overbased metallic detergent is 100 mgKOH/g or more, preferably 150 to 500 mgKOH/g, more preferably 200 to 450 mgKOH/g.

As used herein, the "base number" means the base number measured by the perchloric acid method according to chapter 9 of "Petroleum products and lubricating oils—Neutralization value test method" of JIS K2501:2003.

[Ashless Dispersant]

Examples of the ashless dispersant to be used in an aspect of the present invention include boron-free succinimides such as boron-free alkenylsuccinimide, boron-containing succinimides such as boron-containing alkenylsuccinimide, benzylamines, boron-containing benzylamines, succinic acid esters, and monovalent or divalent carboxylic acid amides typified by fatty acids or succinic acid.

One of these ashless dispersants may be used alone, or two or more of them may be used in combination.

[Metal Deactivator]

Examples of the metal deactivator to be used in an aspect of the present invention include benzotriazole compounds, tolyltriazole compounds, imidazole compounds, and pyrimidine compounds.

One of these metal deactivators may be used alone, or two or more of them may be used in combination.

[Friction Modifier]

Examples of the friction modifier to be used in an aspect of the present invention include molybdenum friction modifiers such as molybdenum dithiocarbamate (MoDTC), molybdenum dithiophosphate (MoDTP), and amine salt of molybdenum acid; ashless friction modifiers such as aliphatic amines, fatty acid esters, fatty acid amides, fatty acids, aliphatic alcohols, and aliphatic ethers having at least one alkyl group or alkenyl group having 6 to 30 carbon atoms in a molecule; fats and oils, amines, amides, and sulfurized esters.

One of these friction modifiers may be used alone, or two or more of them may be used in combination.

[Rust Inhibitor]

Examples of the rust inhibitor to be used in an aspect of the present invention include fatty acids, alkenyl succinic acid half esters, fatty acid soaps, alkyl sulfonates, polyhydric alcohols fatty acid esters, fatty acid amines, oxidized paraffins, and alkyl polyoxyethylene ethers.

One of these rust inhibitors may be used alone, or two or more of them may be used in combination.

[Defoamer]

Examples of the defoamer to be used in an aspect of the present invention include silicone oils, fluorosilicone oils, and fluoroalkyl ethers.

One of these defoamers may be used alone, or two or more of them may be used in combination.

[Properties and Characteristics of Lubricating Oil Composition]

The lubricating oil composition according to an aspect of the present invention comprises the lubricant base oil having a natural origin content of 100% and thus can be a lubricating oil composition that reduces the environmental impact upon disposal.

The lubricating oil composition according to an aspect of the present invention may have a natural origin content of less than 100% by containing an additive for lubricating oil. However, for achieving a lubricating oil composition that reduces the environmental impact upon disposal, the natural origin content of the lubricating oil composition according to an aspect of the present invention is preferably 80% or more, more preferably 85% or more, further preferably 90% or more, furthermore preferably 95% or more, particularly preferably 978 or more.

The kinematic viscosity at 40° C. of the lubricating oil composition according to an aspect of the present invention is appropriately adjusted according to the application and may be 4.0 $mm^2/s$ or more, 4.2 $mm^2/s$ or more, 4.5 $mm^2/s$ or more, 5.0 $mm^2/s$ or more, 5.2 $mm^2/s$ or more, 5.5 $mm^2/s$ or more, 6.0 $mm^2/s$ or more, 6.2 $mm^2/s$ or more, 6.5 $mm^2/s$ or more, 7.0 $mm^2/s$ or more, 7.5 $mm^2/s$ or more, 8.0 $mm^2/s$ or more, 8.5 $mm^2/s$ or more, 9.0 $mm^2/s$ or more, 9.5 $mm^2/s$ or more, or 10.0 $mm^2/s$ or more, and 100 $mm^2/s$ or less, 90 $mm^2/s$ or less, 80 $mm^2/s$ or less, 70 $mm^2/s$ or less, 60 $mm^2/s$ or less, 50 $mm^2/s$ or less, 40 $mm^2/s$ or less, 35 $mm^2/s$ or less, 30 $mm^2/s$ or less, 25 $mm^2/s$ or less, or 20 $mm^2/s$ or less.

The kinematic viscosity at 100° C. of the lubricating oil composition according to an aspect of the present invention is appropriately adjusted according to the application and may be 1.0 $mm^2/s$ or more, 1.5 $mm^2/s$ or more, 2.0 $mm^2/s$ or more, 2.2 $mm^2/s$ or more, 2.5 $mm^2/s$ or more, 2.7 $mm^2/s$ or more, or 3.0 $mm^2/s$ or more, and 10 $mm^2/s$ or less, 9.0 $mm^2/s$ or less, 8.0 $mm^2/s$ or less, 7.0 $mm^2/s$ or less, 6.0 $mm^2/s$ or less, 5.0 $mm^2/s$ or less, 4.5 $mm^2/s$ or less, 4.2 $mm^2/s$ or less, 4.0 $mm^2/s$ or less, 3.8 $mm^2/s$ or less, or 3.5 $mm^2/s$ or less.

The viscosity index of the lubricating oil composition according to an aspect of the present invention may be 70 or more, 80 or more, 85 or more, 90 or more, 95 or more, 100 or more, 105 or more, 110 or more, 115 or more, 120 or more, 125 or more, or 130 or more.

The pour point of the lubricating oil composition according to an aspect of the present invention is preferably 0° C. or less, more preferably −5° C. or less, more preferably −10° C. or less, further preferably −20° C. or less, further preferably −25° C. or less, furthermore preferably −30° C. or less, furthermore preferably −35° C. or less, particularly preferably −40° C. or less.

The flash point of the lubricating oil composition according to an aspect of the present invention may be preferably 170° C. or more, more preferably 174° C. or more, more preferably 180° C. or more, more preferably 184° C. or more, further preferably 190° C. or more, further preferably 194° C. or more, further preferably 200° C. or more, furthermore preferably 204° C. or more, furthermore preferably 210° C. or more, furthermore preferably 214° C. or more, particularly preferably 220° C. or more, and 400° C. or less, 380° C. or less, 350° C. or less, 330° C. or less, 320° C. or less, 310° C. or less, or 300° C. or less.

The volume change rate of an acrylic rubber for test, as measured by immersing the acrylic rubber for test in the lubricating oil composition according to an aspect of the present invention under conditions at 150° C. for 72 hours in accordance with JIS K6258 is preferably less than 208, more preferably 18% or less, more preferably 15% or less, further preferably 13% or less, further preferably 10% or less, furthermore preferably 8% or less, particularly preferably 7% or less.

The foam volumes immediately after and 10 minutes of the lubricating oil composition according to an aspect of the present invention, as measured after a foaming test at room temperature (24° C.) under conditions of sequences I, II, and III defined in JIS K2518, are each independently preferably 5 mL or less, more preferably 3 mL or less, further preferably 1 mL or less, furthermore preferably 0 mL (no foaming was confirmed).

The value of the foam volume means a value measured by conducting the foaming test described in Examples below.

The discoloration number of the lubricating oil composition according to an aspect of the present invention, as specified based on the description of "Table 1: Corrosion classification according to copper plate corrosion standard" of JIS K2513 showing the degree of discoloration of a copper plate after the copper plate corrosion test at 100° C. for 3 hours in accordance with JIS K2513, is preferably 2c or less, more preferably 2b or less, further preferably 2a or less, furthermore preferably 1b or less.

The discoloration number means a value specified by conducting the copper plate corrosion test described in Examples below based on "Table 1: Corrosion classification according to copper plate corrosion standard" of JIS K2513.

The voltage of the lubricating oil composition according to an aspect of the present invention, when dielectric breakdown occurs, and insulation is lost by conducting a dielectric breakdown voltage test in accordance with JIS C2101, is preferably 50 kV or more, more preferably 60 kV or more, further preferably 70 kV or more, furthermore preferably 80 kV or more, particularly preferably 85 kV or more.

The value of the voltage means a value measured by conducting the dielectric breakdown voltage test described in Examples below.

The diameter of the wear mark, as measured by conducting a shell wear test under the test conditions at a test temperature of 80° C., a load of 392 N, and a rotational speed of 1800 rpm, for a test time of 30 minutes according to ASTM D4172 using the lubricating oil composition according to an aspect of the present invention, is preferably 1.00 mm or less, more preferably 0.90 mm or less, more preferably 0.80 mm or less, further preferably 0.70 mm or less, furthermore preferably 0.60 mm or less, particularly preferably 0.50 mm or less.

The value of the diameter of the wear mark means a value measured by conducting the shell wear test described in Examples below.

[Applications of Lubricating Oil Composition]

The lubricating oil composition according to a preferable aspect of the present invention is excellent in various lubricating properties, while being a lubricating oil composition that reduces the environmental impact upon disposal.

In consideration of such properties, the lubricating oil composition according to an aspect of the present invention can be preferably used, for example, for lubrication in electric drive units, engines, transmissions, decelerators, compressors, and mechanisms such as torque converters, wet clutches, gear bearing mechanisms, oil pumps, and hydraulic control mechanisms that are incorporated in various hydraulic systems. Further, due to excellent cooling and insulation properties, it can be suitably used for cooling and insulation of motors or batteries.

EXAMPLES

Next, the present invention will be described in more detail with reference to Examples; however, the present invention is not limited in any way by these Examples. The methods for measuring or calculating various properties are as follows.

(1) Natural Origin Content

It was calculated in accordance with ISO 16128.

(2) Kinematic Viscosity and Viscosity Index

They were measured and calculated in accordance with JIS K2283:2000.

(3) Pour Point

It was measured in accordance with JIS K2269.

(4) Flash Point

It was measured by the Cleveland Open Cup method (COC method) in accordance with JIS K2265-4 (Determination of Flash Point—Part 4: Cleveland Open Cup Method).

(5) Volume Change Rate of Acrylic Rubber

A rubber immersion test in accordance with JIS K6258 was conducted. Specifically, it was measured by immersing a test piece of acrylic rubber for test (product name: "T303", available from NOK CORPORATION) in a lubricant base oil to be measured under conditions at an immersion temperature of 150° C. for an immersion time of 72 hours. Then, the volume of the test piece was measured before and after the test, and the volume change rate was calculated from the following formula.

[Volume change rate (%)]=([Volume of test piece after test]−[Volume of test piece before test])/[Volume of test piece before test]×100

(Lubricant Base Oil)

Examples 1 to 4 and Comparative Examples 1 to 3

The ester compounds synthesized from carboxylic acid components and alcohol components shown in Table 1 were used as lubricant base oils (1) to (7), the natural origin content was calculated, and various properties required for lubricant base oils were measured according to the aforementioned methods. Table 1 shows these results.

Reference Examples 1 and 2

Using 60 N mineral oil as a lubricant base oil (8) in Reference Example 1 and 100 N mineral oil as a lubricant base oil (9) in Reference Example 2, the natural origin content was calculated, and various properties were measured according to the aforementioned methods. Table 1 shows these results.

[Table 1]

TABLE 1

| | | Example 1 Lubricant base oil (1) | Example 2 Lubricant base oil (2) | Example 3 Lubricant base oil (3) | Example 4 Lubricant base oil (4) |
|---|---|---|---|---|---|
| Compound name | | Methylheptyl isostearate | Methylheptyl palmitate | Methylheptyl myristate | Methylheptyl laurate |
| Molecular formula of compound | | $C_{26}H_{52}O_2$ | $C_{24}H_{48}O_2$ | $C_{22}H_{44}O_2$ | $C_{20}H_{40}O_2$ |
| Group of $R^1$ in formula (1) | | C17 branched alkyl | C15 linear alkyl | C13 linear alkyl | C11 linear alkyl |
| Group of $R^2$ in formula (1) | | C8 branched alkyl | C8 branched alkyl | C8 branched alkyl | C8 branched alkyl |
| Carboxylic acid component | | Isostearic acid (rapeseed derived) | Palmitic acid (palm/coco derived) | Myristic acid (palm derived) | Lauric acid (palm/coco derived) |
| Alcohol component | | 2-Octanol (castor bean derived) | 2-Octanol (castor bean derived) | 2-Octanol (castor bean derived) | 2-Octanol (castor bean derived) |
| Natural origin content | % | 100 | 100 | 100 | 100 |
| Kinematic viscosity at 40° C. | $mm^2/s$ | 11.4 | 8.6 | 6.8 | 5.294 |
| Kinematic viscosity at 100° C. | $mm^2/s$ | 3.1 | 2.6 | 2.2 | 1.844 |
| Viscosity index | — | 133 | 157 | 148 | — |
| Pour point | ° C. | −40.0 | 0.0 | −12.5 | −25.0 |
| Flash point (COC) | ° C. | 220 | 210 | 200 | 184 |
| Volume change rate of acrylic rubber | % | 6 | 6 | 8 | 13 |

| | | Comparative Example 1 Lubricant base oil (5) | Comparative Example 2 Lubricant base oil (6) | Comparative Example 3 Lubricant base oil (7) | Reference Example 1 Lubricant base oil (8) | Reference Example 2 Lubricant base oil (9) |
|---|---|---|---|---|---|---|
| Compound name | | 2-Ethylhexyl palmitate | Butyl laurate | Di(2-ethylhexyl) sebacate | 60N mineral oil | 100N mineral oil |
| Molecular formula of compound | | $C_{24}H_{48}O_2$ | $C_{16}H_{32}O_2$ | $C_{26}H_{50}O_4$ | — | — |
| Group of $R^1$ in formula (1) | | C15 linear alkyl | C11 linear alkyl | — | — | — |
| Group of $R^2$ in formula (1) | | C8 branched alkyl | C4 linear alkyl | — | — | — |
| Carboxylic acid component | | Palmitic acid (palm/coco derived) | Lauric acid (palm/coco derived) | Sebacic acid (castor bean derived) | — | — |
| Alcohol component | | 2-Ethylhexanol (petroleum derived) | Butanol (petroleum derived) | 2-Ethylhexanol (petroleum derived) | — | — |
| Natural origin content | % | 65 | 71 | 39 | 0 | 0 |
| Kinematic viscosity at 40° C. | $mm^2/s$ | 8.3 | 3.4 | 11.6 | 7.9 | 19.8 |
| Kinematic viscosity at 100° C. | $mm^2/s$ | 2.6 | 1.4 | 3.2 | 2.3 | 4.3 |
| Viscosity index | — | 165 | — | 147 | 104 | 122 |
| Pour point | ° C. | 0.0 | −10.0 | −60.0 | −32.5 | −20.0 |
| Flash point (COC) | ° C. | 210 | 168 | 224 | 164 | 230 |
| Volume change rate of acrylic rubber | % | 6 | 32 | 21 | 3 | 2 |

As shown in Table 1, the lubricant base oils (1) to (4) of Examples 1 to 4 had a natural origin content of 100% and can be said to be lubricant base oils with reduced environmental impact upon disposal. Further, it was confirmed that the lubricant base oils (1) to (4) had similar properties to those of the lubricant base oils (8) to (9) of Reference Examples 1 and 2.

Meanwhile, the lubricant base oils (5) to (7) of Comparative Examples 1 to 3 had a low natural origin content and can be said to be lubricant base oils that are concerned about the environmental impact upon disposal. Further, the lubricant base oils (6) and (7) had a volume change rate of acrylic rubber of 20% or more and had a problem in rubber swelling resistance.

(Lubricating Oil Composition)

Example 5 and Reference Example 3

In Example 5, the lubricant base oil (1) of Example 1 and various additive with a content shown in Table 2 were added to prepare a lubricating oil composition.

Further, in Reference Example 3, the 60 N mineral oil of the lubricant base oil (8) of Reference Example 1, the 100 N mineral oil of the lubricant base oil (9) of Reference Example 2, a pour point depressant, and various additives with a content shown in Table 2 were added to prepare a lubricating oil composition.

Components used in the preparation of these lubricating oil compositions were as follows.

Lubricant base oil (1): Methylheptyl isostearate shown in Table 1 as the lubricant base oil (1) of Example 1.

Lubricant base oil (8): 60 N mineral oil shown in Table 1 as the lubricant base oil (8) of Reference Example 1.

Lubricant base oil (9): 100 N mineral oil shown in Table 1 as the lubricant base oil (9) of Reference Example 2.

Pour point depressant: Polymethacrylate (PMA) pour point depressant.

Various additives: Additive mixture composed of phosphite ester, thiadiazole, calcium sulfonate (base number: 300 mgKOH/g), polybutenyl succinimide, benzotriazole, and silicone defoamer.

Various properties of the lubricating oil compositions prepared were measured by the aforementioned methods, and various tests (1) to (4) below were conducted. Table 2 shows these results.

(1) Foaming Test

Each lubricating oil composition to be measured was subjected to a foaming test under conditions at room temperature (24° C.) according to sequences I, II, and III defined in JIS K2518, to measure the foam volumes immediately after and 10 minutes after the test start. It can be said that the smaller the foam volume, the more excellent the defoaming property of the lubricating oil composition.

(2) Copper Plate Corrosion Test

The discoloration number was specified by conducting the copper plate corrosion test at 100° C. for 3 hours in accordance with JIS K2513 based on the description of "Table 1: Corrosion classification according to copper plate corrosion standard" of JIS K2513 for the degree of discoloration of a copper plate after the test. It can be said that the smaller the discoloration number, the more excellent the corrosion resistance of the lubricating oil composition.

(3) Dielectric Breakdown Voltage Test

A dielectric breakdown voltage test was conducted in accordance with JIS C2101, to measure the voltage (unit: kV) when dielectric breakdown occurs, and insulation is lost. It can be said that the larger the voltage, the more excellent the insulating properties of the lubricating oil composition.

(4) Shell Wear Test

The diameter of the wear mark (unit: mm) under test conditions at a test temperature of 80° C., a load of 392N, and a rotational speed of 1800 rpm for a test time of 30 minutes was measured according to ASTM D4172. It can be said that the smaller the value of the wear scar diameter, the more excellent wear resistance between metals of the lubricating oil composition.

[Table 2]

TABLE 2

| | | | | Example 5 | Reference Example 3 |
|---|---|---|---|---|---|
| Composition of lubricating oil composition | Lubricant base oil (1) | Methylheptyl isostearate | mass % | 98.0 | — |
| | Lubricant base oil (8) | 60N mineral oil | mass % | — | 50.0 |
| | Lubricant base oil (9) | 100N mineral oil | mass % | — | 47.9 |
| | Pour point depressant | PMA pour point depressant | mass % | — | 0.1 |
| | Various additives | Additive mixture | mass % | 2.0 | 2.0 |
| | Total | | mass % | 100.0 | 100.0 |
| Properties of lubricating oil composition | Natural origin content | | mass % | 98 | 0 |
| | Kinematic viscosity at 40° C. | | $mm^2/s$ | 12.1 | 12.6 |
| | Kinematic viscosity at 100° C. | | $mm^2/s$ | 3.2 | 3.2 |
| | Viscosity index | | — | 133 | 119 |
| | Pour point | | ° C. | −40.0 | −47.5 |
| | Flash point (COC) | | ° C. | 220 | 184 |
| | Volume change rate of acrylic rubber | | % | 6 | 3 |
| Evaluation test | Foaming test | Sequence I foam volume (immediately after test to 10 minutes after test) | mL | 0-0 | 0-0 |
| | | Sequence II foam volume (immediately after test to 10 minutes after test) | mL | 0-0 | 0-0 |
| | | Sequence III foam volume (immediately after test to 10 minutes after test) | mL | 0-0 | 0-0 |
| | Copper plate corrosion test | Discoloration number | — | 1b | 1b |
| | Dielectric breakdown voltage test | Voltage when dielectric breakdown occurs | kV | 86 | 85 |
| | Shell wear test | Diameter of wear mark | mm | 0.49 | 0.78 |

As shown in Table 2, the lubricating oil composition prepared in Example 5 had a high natural origin content of 98% and can be said to be a lubricating oil composition with reduced environmental impact upon disposal. Further, it was confirmed that various lubricating performances of the lubricating oil composition of Example 5 are comparable to those of the lubricating oil composition of Reference Example 3 and have various good lubricating properties required for general lubricating oil compositions.

The invention claimed is:

1. A lubricant base oil, comprising:

a monoester compound having comprising a branched structure and carbon atoms in a range of from 24 to 26, wherein the lubricant base oil has a natural origin content (ISO 16128) of 100%, wherein the lubricant base oil has a kinematic viscosity at 40° C. in a range of from 7.0 to 20.0 $mm^2/s$, wherein the monoester compound is of formula (1):

(1)

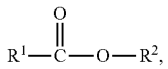

wherein $R^1$ and $R^2$ are each independently a hydrocarbon group, wherein at least one of $R^1$ and $R^2$ is a branched hydrocarbon group, wherein a total number of carbon atoms of $R^1$ and $R^2$ is in a range of from 23 to 25.

wherein a number of carbon atoms of $R^1$ is 24 or less, and wherein a number of carbon atoms of $R^2$ is 20 or less.

2. The lubricant base oil of claim 1, wherein, in the compound of formula (1).

$R^1$ is an alkyl group or alkenyl group having 15 or more carbon atoms, $R^2$ is an alkyl group or alkenyl group having 5 or more carbon atoms, and at least one of R1 and R2 is a branched alkyl group or a branched alkenyl group.

3. The lubricant base oil of claim 1, wherein $R^1$ and $R^2$ in formula (1) are each independently a branched alkyl group or a branched alkenyl group.

4. The lubricant base oil of claim 1, wherein a pour point of the lubricant base oil is 0° C. or less.

5. The lubricant base oil of claim 1, wherein a volume change rate of an acrylic rubber for test, as measured by immersing the acrylic rubber for test in the lubricant base oil under conditions at 150° C. for 72 hours in accordance with JIS K6258, is less than 20%.

6. A lubricating oil composition, comprising:

the lubricant base oil of claim 1.

7. The composition of claim 6, further comprising:

a pour point depressant;

a viscosity index improver;

an antioxidant;

an extreme pressure agent;

a metallic detergent;

an ashless dispersant;

a metal deactivator;

a friction modifier;

a rust inhibitor; and/or a defoamer.

8. The lubricant base oil of claim 1, wherein $R^1$ and $R^2$ in formula (1) are each independently a branched alkyl group.

9. The lubricant base oil of claim 1, wherein $R^1$ and $R^2$ in formula (1) are each independently a branched alkenyl group.

10. The lubricant base oil of claim 1, wherein the lubricant base oil has a kinematic viscosity at 40° C. in a range of from 7.04 to 11.4 $mm^2/s$.

11. The lubricant base oil of claim 1, wherein the branched hydrocarbon group for at least one of $R^1$ and $R^2$ is independently 1-methylheptyl, 1-methyloctyl, 1,1-dimethylheptyl, 1-methyldecyl, 1-methylundecyl, 1-methyldodecyl, 1-methyltridecyl, 1-methyltetradecyl, 1-methylpentadecyl, 1-methylhexadecyl, 1-methylheptadecyl, or 1-methyloctadecyl.

12. The lubricant base oil of claim 1, wherein the monoester compound comprises, in esterified form, 2-octanol.

13. The lubricant base oil of claim 1, wherein $R^1$ in formula (1) is C17 branched alkyl, C15 linear alkyl, C13 linear alkyl, or C11 linear alkyl, and wherein $R^2$ in formula (1) is C8 branched alkyl.

14. The lubricant base oil of claim 1, wherein the monoester compound comprises, in esterified form, isostearic acid, palmitic acid, myristic acid, or lauric acid.

15. The lubricant base oil of claim 1, wherein the monoester compound comprises methylheptyl isostearate or methylheptyl palmitate.

16. The lubricant base oil of claim 1, wherein a monoester compound comprises the carbon atoms in a range of from 24 to 25.

17. The lubricant base oil of claim 1, wherein a monoester compound comprises the carbon atoms in a range of from 25 to 26.

18. The lubricant base oil of claim 1, wherein a monoester compound comprises 25 of the carbon atoms.

* * * * *